(12) United States Patent
Yoneda

(10) Patent No.: US 6,569,334 B1
(45) Date of Patent: May 27, 2003

(54) METHOD OF HIGH-CONCENTRATION CULTURE OF NITRIFYING BACTERIA OR DENITRIFYING BACTERIA CONTAINED IN ACTIVATED SLUDGE, CULTURE PROMOTER TO BE USED IN HIGH-CONCENTRATION CULTURE METHOD OF NITRIFYING BACTERIA, AND METHOD OF WEIGHT LOSS TREATMENT OF ACTIVATED SLUDGE

(75) Inventor: Satoshi Yoneda, Toyonaka (JP)

(73) Assignee: Bicom Corporation, Osaka (JP)

( * ) Notice: Subject to any disclaimer, the term of this patent is extended or adjusted under 35 U.S.C. 154(b) by 0 days.

(21) Appl. No.: 10/009,608

(22) PCT Filed: Jun. 5, 2000

(86) PCT No.: PCT/JP00/03656

§ 371 (c)(1), (2), (4) Date: Dec. 10, 2001

(87) PCT Pub. No.: WO00/77171

PCT Pub. Date: Dec. 21, 2000

(30) Foreign Application Priority Data

Jun. 10, 1999 (JP) .......................................... 11/163479

(51) Int. Cl.[7] .................................................. C02F 3/00
(52) U.S. Cl. ........................ 210/610; 210/613; 210/623; 210/742; 210/743; 210/758
(58) Field of Search ................................ 210/610, 612, 210/613, 614, 620–628, 743, 742, 758

(56) References Cited

FOREIGN PATENT DOCUMENTS

| JP | 6-206093 | 7/1994 |
| JP | 6-304593 | 11/1994 |
| JP | 7-299495 | 11/1995 |

*Primary Examiner*—Chester T. Barry
(74) *Attorney, Agent, or Firm*—Jordan & Hamburg LLP

(57) ABSTRACT

A method for incubation of nitrifying bacteria in a high concentration which are contained in small amount in activated sludge includes subjecting the activated sludge to nitrification and acclimation culture for about one to two months using a sludge-treated waste liquid such as dehydrate sludge filtrate and digested eluate under such a condition that the dissolved oxygen is 2–4 mg/liter, the pH is 7.5–8.5 and the temperature is 25–35° C. and, at the same time, constantly maintaining the pH within the pH range of 7.7–8.5 by addition of an incubation promoter comprising a mixture of sodium carbonate and sodium hydrogen carbonate.

22 Claims, 8 Drawing Sheets

METHOD OF HIGH-CONCENTRATION CULTURE OF NITRIFYING BACTERIA OR DENITRIFYING BACTERIA CONTAINED IN ACTIVATED SLUDGE, CULTURE PROMOTER TO BE USED IN HIGH-CONCENTRATION CULTURE METHOD OF NITRIFYING BACTERIA, AND METHOD OF WEIGHT LOSS TREATMENT OF ACTIVATED SLUDGE

TECHNICAL FIELD

The present invention relates to a method for a high-concentration incubation of nitrifying bacteria (marine nitrifying bacteria and freshwater nitrifying bacteria) or denitrifying bacteria (marine denitrifying bacteria and freshwater denitrifying bacteria) using activated sludge as a raw material, to an incubation promoter used therefor and to a method for a weight reducing treatment of the activated sludge.

BACKGROUND OF THE INVENTION

With regard to a method for the elimination of pollution by nitrogen, particularly by ammonia, in an aqueous system, there are a physicochemical method and a method utilizing organisms.

Examples of the physicochemical method are an ammonia stripping method, a discontinuous point chlorine injection method, a zeolite method and an ion-exchange method.

However, in those methods, there are many problems in view of the efficiency and the secondary environmental pollution due to by-products.

On the other hand, with regard to a method utilizing organisms, it has been well known that a method by treating with microorganism using nitrifying bacteria (ammonia oxidizing bacteria and nitrite oxidizing bacteria) and denitrifying bacteria (nitrate oxidizing bacteria) is most useful. Harmful residual nitrogen in an aqueous system is accumulated as nitrate ion as a result of action of nitrifying bacteria under aerobic environment, reduced to safe nitrogen gas by denitrifying bacteria under anaerobic environment and exhausted into air.

However, nitrifying bacteria have a slow growing rate and do not live by means of formation of colonies and, therefore, there has been no report on the success in a high-concentration incubation in a large quantity in an industrial scale up to the present time where more than one hundred years have passed since their presence was confirmed.

Thus, the conventional incubating method is in a small scale of a test tube level with an object of pure culture and, in the case of incubation of about two months, the result is that the medium in a flask is not suspended whereby it is not an incubating method which can be applied in industry.

To be more specific, when nitrification begins in the incubation of nitrifying bacteria, pH lowers and, until now, no method for an effective increase in the pH has been known. On the other hand, carbon sources decrease as a result of nitrification and, until now, carbon dioxide has been used for supplying the carbon source. Although it is of course possible to prevent the exhaustion of carbon sources when carbon dioxide is supplied, the above-mentioned lowering of the pH further proceeds by that whereupon activity of the nitrifying bacteria stops and that is a limit of the growth of the bacteria.

DISCLOSURE OF THE INVENTION

Reference to the Deposited Biological Materials (1) Name of the Depository Institution: Patent Microorganism Depository Center, National Institute of Bioscience and Human Technology, Agency of Industrial Science and Technology, MITI Address: Postal Code 305-0046
1-1-3 Higashi, Tsukuba-shi, Ibaraki-ken, Japan
(Telephone: 0298 54 6029)
(2) Deposited Date: Apr. 27, 2000
(3) Accession Number: FERM BP-7150

The present invention relates to a method for the incubation of nitrifying bacteria in a high concentration which are contained in a few amounts in activated sludge such as sewage sludge and excrement sludge and is a method for a high-concentration incubation of nitrifying bacteria which is characterized in that the above-mentioned activated sludge is subjected to nitrification and acclimation culture by a liquid containing $NH_4$—N for a predetermined period under such a condition that that dissolved oxygen is not less than 2 mg/liter, pH is 7.0–9.0 and temperature is 20–40° C. and, at the same time, the pH which is apt to tend to an acid side during the process of acclimation culture is constantly maintained within the above-mentioned range by addition of an incubation promoter comprising a mixture of sodium carbonate and sodium hydrogen carbonate whereby the nitrifying bacteria contained in the above-mentioned sludge are subjected to acclimation culture and are accumulated.

The present further relates to a method for the incubation of denitrifying bacteria in a high concentration which are contained in a few amounts in activated sludge such as sewage sludge and excrement sludge and is a method for a high-concentration incubation of denitrifying bacteria which is characterized in that the above-mentioned activated sludge is subjected to denitrification and acclimation culture by a liquid containing $NO_3$—N for a predetermined period under such a condition that dissolved oxygen is not more than 2 mg/liter, pH is 6.0–9.0, temperature is 10–40° C. and ROH (R is $CH_3$— and/or $C_2H_5$—) is present as an external carbon source whereby the denitrifying bacteria contained in the above-mentioned activated sludge are subjected to acclimation culture and are accumulated.

In accordance with the present invention, it is now possible to incubate the nitrifying bacteria or the denitrifying bacteria in a large quantity and also in a high concentration.

Activated Sludge

Examples of the activated sludge used in the present invention are sewage sludge and excrement sludge. They may be either subjected to a diluting treatment with fresh water or subjected to a diluting treatment with sea water but, when nitrifying bacteria or denitrifying bacteria are incubated using a sludge diluted with sea water as a raw material, marine nitrifying bacteria and marine denitrifying bacteria which are of scarcity values can be obtained in large quantities and, therefore, it is appropriate to use an activated sludge which is diluted with sea water.

To be more precise, in natural sea water, there are marine nitrifying bacteria which are believed to have higher resistance to salt than freshwater nitrifying bacteria but, since their amount is very small and their separation in a pure state is difficult, studies thereof are in the rear of freshwater nitrifying bacteria. However, in accordance with the incubating method of the present invention, the activated sludge which is diluted with sea water as mentioned already is used whereby it is possible to prepare the marine nitrifying bacteria of a high concentration. The marine nitrifying bacteria are equipped with multi-layered cell walls and have a strong resistance to changes in osmotic pressure and to various chemical substances which inhibit the growth.

Incubating (Acclimation Culture) Conditions for Nitrifying Bacteria

In the incubation of nitrifying bacteria contained in activated sludge, the said activated sludge is subjected to nitrification and acclimation culture for a predetermined period (for example, for one month, two months or three months) using waste liquid in sludge treatment such as dehydrated filtrate of sludge and (anaerobic) digested eluate and, since the nitrification and acclimation culture are to be carried out aerobically, it is necessary to make the dissolved oxygen (DO) at that time 2 mg/liter or more. However, it has been firstly found by the experiment at this time that, when the dissolved oxygen concentration is made too high, the growing speed rather tends to lower. That will be illustrated in detail as hereunder.

The more the dissolved oxygen, the quicker the nitrifying speed by the nitrifying bacteria. Therefore, it has been believed that the more the dissolved oxygen, the quicker the nitrification and the acclimation culture as well but, quite unexpectedly, it has been found now that speed of the acclimation culture and the accumulation lowers when the dissolved oxygen (DO) is more than about 5 mg/liter. Incidentally, it is most preferred that the dissolved oxygen (DO) concentration is 2–4 mg/liter.

It is also necessary that pH is 7.0–9.0 and (,especially when activated sludge diluted with sea water is used,) the pH is preferably 7.5–8.5 and, more preferably, 7.5–7.8.

With regard to the temperature for incubation, growing speed is high when it is within a range of 20–40° C. and the range of 25–35° C. is more preferred.

Incidentally, during the process of incubation, alkalinity lowers when pH lowers. Thus, oxidation of $NH_4^+$ to $NO_2^-$ by the ammonia oxidizing bacteria and oxidation of $NO_2^-$ to $NO_3^-$ by the nitrite oxidizing bacteria are expressed by the following two formulae (A) and (B). Incidentally, the formula (C) is a formula in terms of the nitrifying bacteria as a whole.

(Ammonia oxidizing bacteria)

$$NH_4^+ + 1.5O_2 \rightarrow NO_2^- + H_2O + 2H^+ \quad (A)$$

(Nitrite oxidizing bacteria)

$$NO_2^- + 0.5O_2 \rightarrow NO_3^- \quad (B)$$

(Mixed system)

$$NH_4^+ + 2.0O_2 \rightarrow NO_3^- + H_2O + 2H^+ \quad (C)$$

From those formulae, it is noted that 4.57 mg $O_2$/mg $NH_4$—N of oxygen are needed for oxidation of $NH_4$—N to $NO_3$—N and that, since hydrogen ion is released as the nitrification reaction proceeds, the alkalinity decreases when the pH of the incubating system lowers. Since the incubating rate decreases as the pH lowers, activity of the microorganism stops as same as in the conventional methods unless the pH is kept at a predetermined value using a buffer or the like.

Accordingly, in the present invention, with a belief that a substance which is a mixture of nonhydride and hydride to give a buffer action is suitable for adjusting the pH which tends to an acid side during the incubating process, we have repeatedly carried out tries-and-errors using many compounds and, as a result, it has been found to be most appropriate to recover the pH by pouring an incubation promoter comprising a combination of sodium carbonate and sodium hydrogen carbonate thereinto.

It has been known that, generally, synthetic reaction of bacterial cells can be expressed by the following formula.

$$4CO_2 + HCO_3^- + NH_4^+ + H_2O \rightarrow C_5H_7NO_2 + 5O_2$$

When that is applied to the biochemical reaction formula of the above-mentioned mixed incubation system (C), the result will be nearly as follows.

$$NH_4^+ + 1.86O_2 + 1.98HCO_3^- \rightarrow 0.021C_5H_7NO_2 + 0.98NO_3^- + 1.04H_2O + 1.88H_2CO_3$$

It is apparent from the above formula that a lot of carbon source is necessary for incubation of nitrifying bacteria even as compared with ammonium ion which is an energy substrate.

As mentioned above, when an incubation promoter comprising a combination of sodium carbonate and sodium hydrogen carbonate is supplied, carbon source for the carbon dioxide assimilation can be supplied at the same time. Illustration will be made as hereunder.

When sodium carbonate is solely used, an effect of rising the lowering pH can be well achieved because the said sodium carbonate is strongly alkaline but, since an effect of rising the pH is big, it cannot be used in a large quantity whereby there is an inconvenience for supplying the carbon source sufficiently. On the other hand, when sodium hydrogen carbonate is solely used, there is no problem in terms of supplying the inorganic carbon source but, in terms of keeping the pH, a large quantity is to be supplied and that is not preferred.

In view of the merit and the disadvantage as such, a mixture of sodium carbonate and sodium hydrogen carbonate is advantageously utilized. When an aqueous solution of those compounds is used, it is now possible that the pH which gradually lowers is kept constant and, at the same time, inorganic carbon source for the carbon dioxide assimilation for an organism can be effectively supplied.

With regard to the compounding ratio of sodium carbonate to sodium hydrogen carbonate in the above-mentioned mixture, the molar ratio of sodium carbonate to sodium hydrogen carbonate is preferably 4–7:4–8 and, to be more specific, a mixed aqueous solution of 0.4–0.7 (mol/liter) of sodium carbonate and 0.4–0.8 (mol/liter) of sodium hydrogen carbonate is effective.

Incidentally, monitoring of the pH of the incubation system maybe carried out either continuously or intermittently. Although it is preferred to utilize a continuous pH monitoring apparatus such as a pH controller, the present invention is not limited thereto but it is also possible to carry out by means of a manual work utilizing a pH indicator such as Phenol Red.

Concentration of ammonia in a solution containing $NH_4$—N is preferably from 100 mg/liter to 300 mg/liter and, more preferably, it is not more than 200 mg/liter. Ammonia is an energy source when ammonia oxidizing bacteria which are chemoautorophic bacteria grow by carrying out the carbon dioxide assimilation but, if it is present too much, that may rather inhibit the growth and the proliferation in some cases. In addition, the nitrite oxidizing bacteria which are contained in activated sludge like ammonia oxidizing bacteria are the bacteria which successively oxidize nitrous acid produced by the ammonia oxidizing bacteria but, due to such a property, they are weak to high concentrations of nitrous acid and, therefore, the initial concentration of ammonia is not able to made too high. Accordingly, when the concentration of ammonia exceeds 300 mg/liter, it is suitable to appropriately dilute it with sea water or fresh water.

Incidentally, as a liquid containing NH$_4$—N, it is preferred to use a waste liquid in sludge treatment such as dehydrated filtrate of sludge and digested eluate produced in a water treatment plant.

When activated sludge is subjected to nitrification and acclimation culture using a waste liquid in a sludge treatment such as dehydrated filtrate of sludge and digested eluate under the above-mentioned incubating conditions, the nitrifying bacteria slightly contained in the said activated sludge can be incubated in a high concentration. In addition to that, it is possible according to the present invention to reduce the activated sludge to an extent of one-third to one-fourth within two months and also to prepare nitrified sludge having a high specific gravity.

In the meanwhile, it has been said that activated sludge contains about 0.35% of nitrifying bacteria. When such an active sludge is used as a raw material and subjected to acclimation culture and accumulated for about two months by a liquid containing NH$_4$—N, amount of the nitrifying bacteria in the said activated sludge increases to an extent of about ten-fold (3.5%). During that process, other sundry bacteria die due to cannibalism because no nutritive source (feed) is provided from outside. As a result thereof, amount of the activated sludge reduces (volume is reduced).

When most of the sundry bacteria die, they become a hardly degradable organic matter having a big specific gravity called "granule" and the nitrifying bacteria attach around it as a nucleus. Such a hardly degradable organic matter to which the nitrifying bacteria are attached is sedimented in the incubating system due to its high specific gravity. In incubating the nitrifying bacteria in a high concentration, the good sedimentation property as mentioned above is essential. Thus, generally speaking, nitrifying bacteria have a light specific gravity and are floated in the pure culture. Therefore, there is a big possibility that nitrifying bacteria are flown out from the incubating system whereby a high-concentration incubation cannot be expected. Accordingly, in a high-concentration incubation, production of the above-mentioned nucleus (the hardly degradable organic matter) is essential and generation of nucleus is not noted in pure culture of the nitrifying bacteria but is noted only when the activated sludge is used as a raw material.

Condition for Incubation (Acclimation Culture) of Denitrifying Bacteria

Incubation of denitrifying bacteria contained in activated sludge is carried out by subjecting the said activated sludge to a denitrifying accumulation culture by a liquid containing NO$_3$—N for a predetermined period (such as for one month, two months or three months).

A denitrifying reaction is a reaction where an organic energy source (which will be mentioned later) as a hydrogen donor is oxidized using molecular oxygen in NO$_3^-$ in a liquid containing NO$_3$—N. Thus, a denitrifying reaction is an oxidation reaction of an organic substance (AH$_2$) in which NO$_3^-$ is a final hydrogen acceptor instead of oxygen and is expressed by the following formula (a simplified formula).

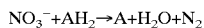

$$NO_3^- + AH_2 \rightarrow A + H_2O + N_2$$

Accordingly, this denitrifying acclimation culture is to be carried out anaerobically and, therefore, the dissolved oxygen (DO) is to be not more than 2 mg/liter, preferably not more than 1 mg/liter or, more preferably, not more than 0.5 mg/liter (in other words, it is necessary to prepare a condition whereby a nitrate respiration is able to take place).

The pH may be within a range of 6.0–9.0 and, rather than otherwise, an alkaline side is preferred. To be more specific, the pH is preferably 6.5–8.5, more preferably 7.0–8.5 and, still more preferably, 7.5–8.5.

With regard to the incubating temperature, activity suddenly lowers when it is lower than 10° C. and, therefore, the said temperature is to be 10–40° C., preferably 15–30° C. and, more preferably, 25–30° C.

With regard to the liquid containing NO$_3$—N, it is possible to use a nitrified and acclimation-cultured liquid which is produced when incubation of nitrifying bacteria is carried out using the activated sludge (refer to the already-mentioned passage).

As mentioned above, an organic matter is to be supplemented from outside as a hydrogen donor and also as a carbon source for the cell synthesis. With regard to such an organic matter from outside, the use of methanol is preferred because it gives quicker growth speed and is less expensive and easily available. Incidentally, it is also possible to use ethanol together with or instead of methanol.

Although there is no particular limitation for the concentration of methanol and/or ethanol to be added, it is preferred that, in terms of methanol, the value of CH$_3$OH (mg/liter)/NO$_3$—N (mg/liter) is 3.0 or more.

BEST MODE FOR CARRYING OUT THE INVENTION

As hereunder, an illustration will be made by way of an example of the present invention although the present invention is not limited thereto.

High-Concentration Incubation of Nitrifying Bacteria (Manufacture of Nitrified Activated Sludge)

Figure 1:
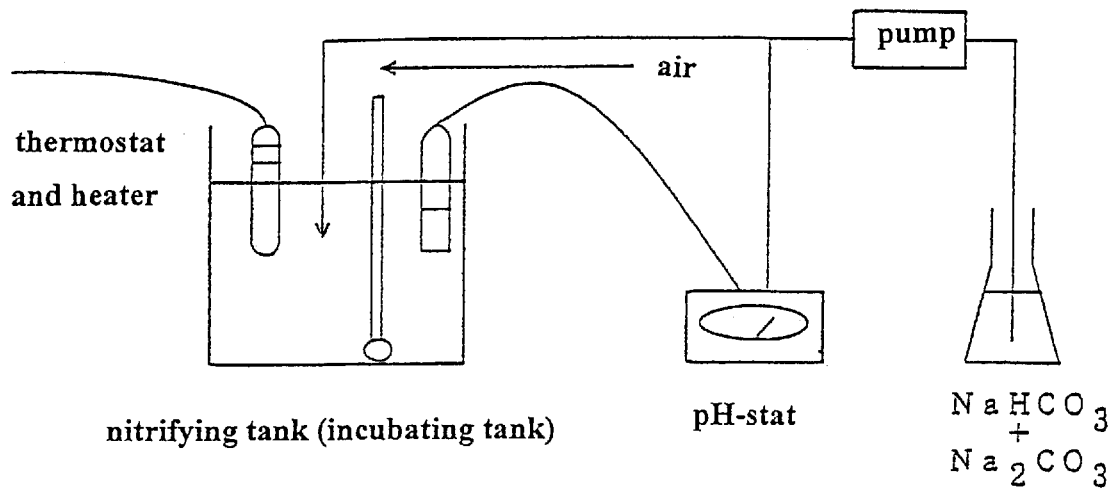
FIG. 1 is a brief illustrative drawing which shows an example of the apparatus for nitrification and acclimation culture of the sludge.

A batch incubation was carried out using an incubation tank (30 liters) of a fill-and-draw type as shown in FIG. 1 where one cycle comprised two days. Thus, seawater-diluted excrement sludge and anaerobic digested eluate (being diluted with sea water to make the $NH_4$—N concentration 100 mg/liter) were placed in an incubation tank and an incubation was carried out where the temperature in the tank was made 27° C. by means of a thermostat and a heater and the pH was kept at 7.5–8.5 by means of a pH controller and an incubation promoter (a buffer comprising 1N $NaHCO_3$ and 0.5N $Na_2CO_3$). (When the initial pH was higher than 8.5, it was adjusted to 8.5 or lower by addition of diluted sulfuric acid.) Further, an aeration amount was adjusted by diffusing balls so as to make the dissolved oxygen (DO) concentration 4 mg/liter.

After one day from the initiation of the aeration, a digested eluate was added again to make the final concentration 100 mg/liter. An operation comprising that, on the second day, an aeration was ceased, that the sludge was precipitated for one hour, that the supernatant liquid was removed, that a digested eluate was poured thereinto and that an aeration was carried out again was repeated.

Since the salt concentration in the starting excrement sludge diluted with sea water corresponded to 80% of that of sea water, acclimation culture was initiated from the stage where the sea water ratio was 80% and, when 100 mg/liter of $NH_4$—N was completely nitrified to $NO_3$—N after one day from the incubation, the sea water ratio was raised to 100%.

During several hours after the initiation of the aeration, the $NH_4$—N concentration decreased linearly and, therefore, the residual $NH_4$—N concentrations after 0, 1, 2, 3 and 4 hour(s) from the initiation of the aeration were measured, the changing rate was determined from the inclination of the section where the $NH_4$—N concentration linearly changed and the value obtained by dividing that by the MLSS concentration was defined as a nitrifying rate (refer to the following formula).

$$RNH_4\text{—}N=[(dNH_4\text{—}N)/dt]\cdot[1/S]$$

$(RNH_4\text{—}N: NH_4\text{—}N$ reducing rate (mg—$NH_4$—N/g-MLSS·hr)

S: concentration of sludge MLSS (g/liter))

SV30 and SVI were measured for activated sludge subjected to seawater acclimation culture and nitrification where acclimation culture was completed after the seawater acclimation culture for about 60 days by means of subjecting to sea water acclimation culture and nitrification whereupon sedimentation characteristics were checked and, at the same time, a state of formation of flocks was observed under an optical microscope.

Figure 2:
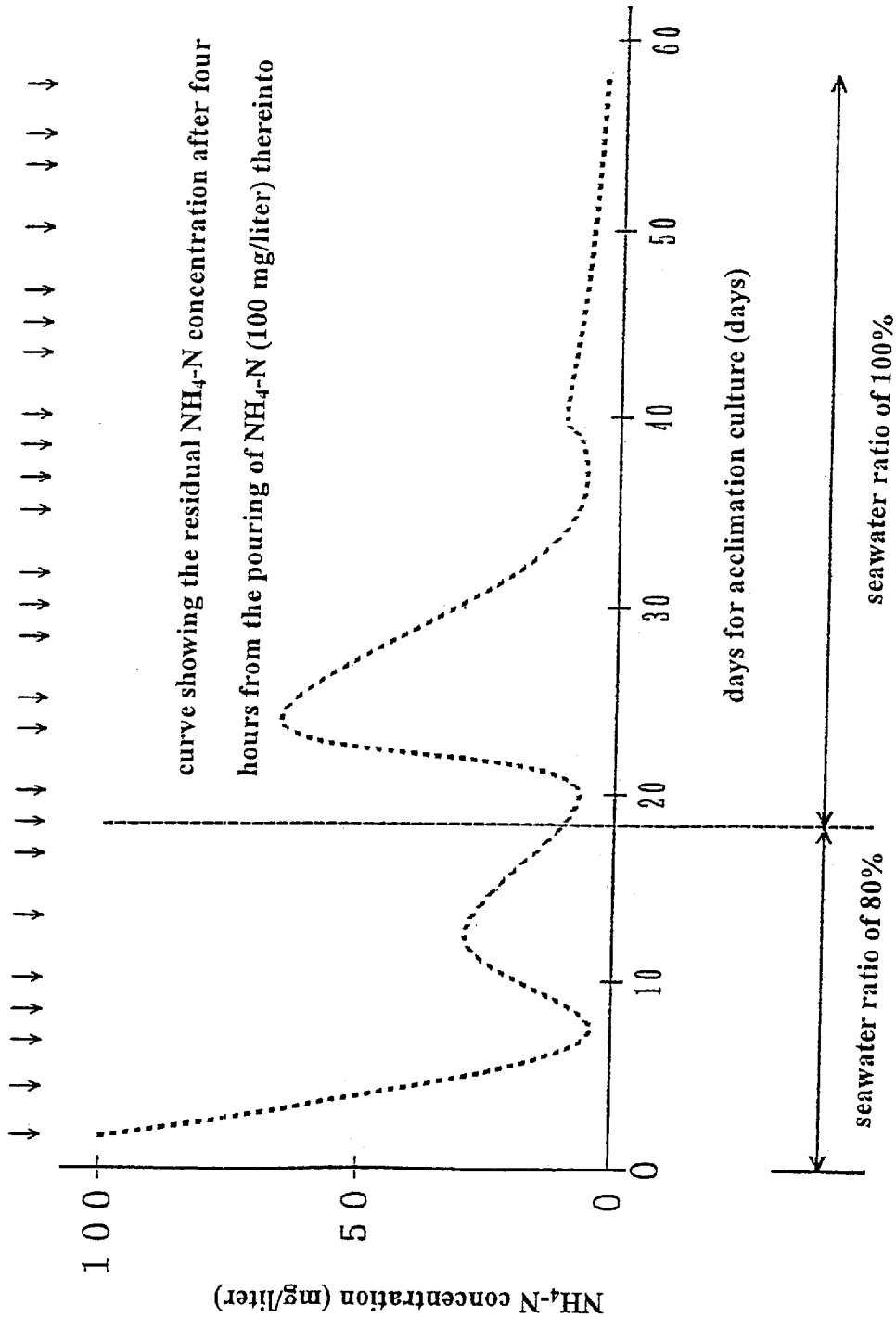
FIG. 2 is a graph which shows the changes in NH$_4$—N concentration in a process of nitrification and acclimation culture of the activated sludge.

Process of acclimation culture of the excrement sludge with sea water is shown in a graph of FIG. 2 (in the said drawing, concentration of $NH_4$—N having the initial concentration of 100 mg/liter after 4 hours is shown).

Figure 3:
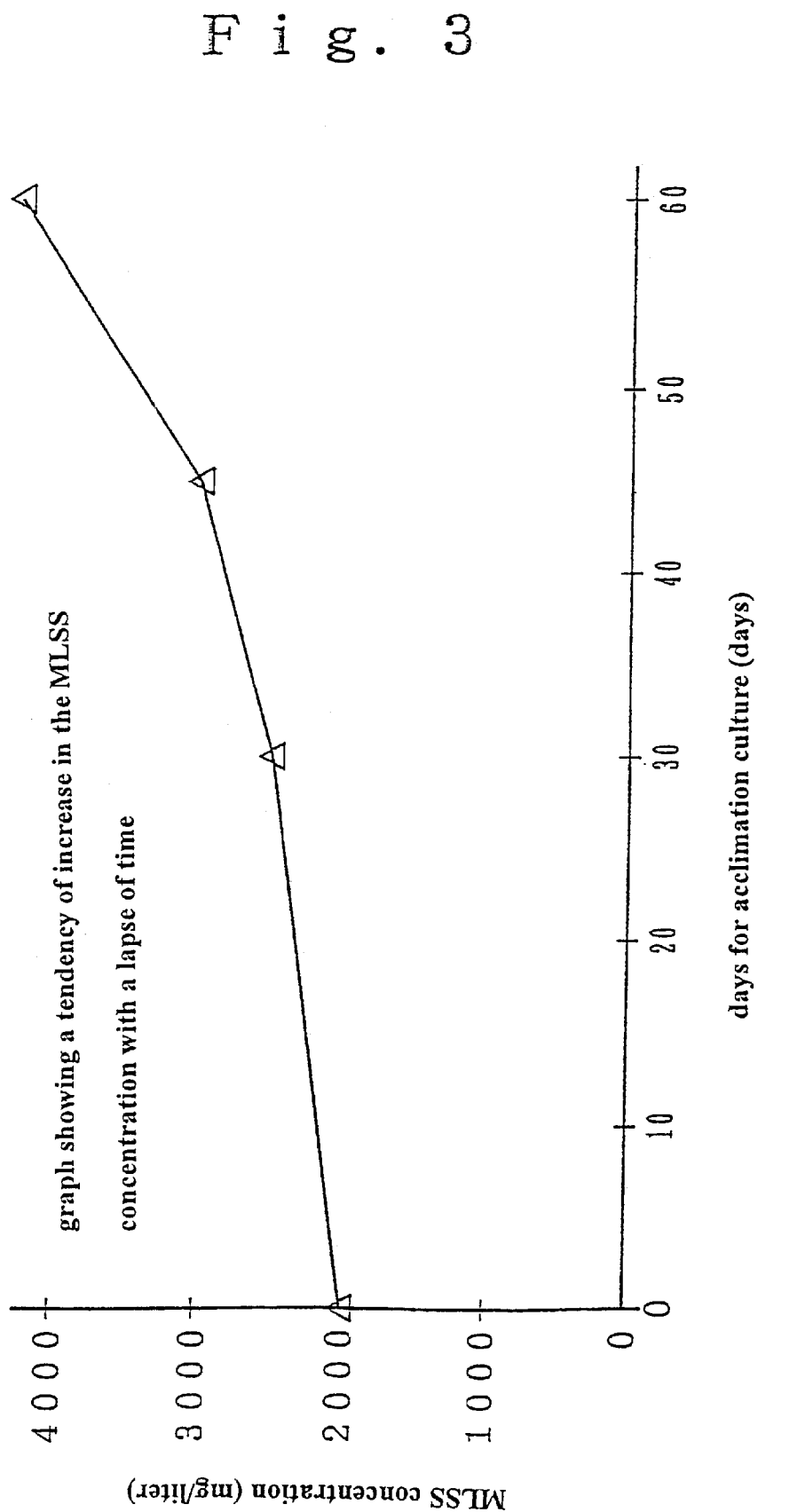
FIG. 3 is a graph which shows the changes in concentration of MLSS with a lapse of time during the process of nitrification and acclimation culture of the activated sludge.

It is understood from the graph of FIG. 2 that, after two months from the initiation of the acclimation culture, it is possible to prepare AMNS which is completely able to nitrify 100 mg/liter (in 100% seawater ratio) of $NH_4$—N within four hours. In order to prevent the loss of nitrified activated sludge by insufficient inorganic carbon source, a pH adjustment by inorganic carbon sources by a combination of $NaHCO_3$ and $Na_2CO_3$ was adopted and, as a result, after two months from the acclimation culture, the MLSS concentration of AMNS was able to be increased, as shown in FIG. 3, to an extent of two-fold as compared with the stage before the acclimation culture.

Nitrification rate of the nitrifying bacteria in AMNS is shown in the following Table 1.

TABLE 1

|  | Nitrifying Rate | SV30 | SVI |
| --- | --- | --- | --- |
| Sludge at Excrement Sewage Plant before Acclimation Culture | 1.35 | — | — |
| Sludge Subjected to Seawater Acclimation Culture and Nitrification (AMNS) | 13.56 | 9% | 42.6 |

*Unit for nitrifying rate: mg-$NH_4$—N/g-MLSS.hr

The existing rate of nitrifying bacteria in the activated sludge has been reported to be about 0.35% and, upon calculation therefrom, it is presumed that the nitrifying bacteria are present in a high concentration (about 3.5%) in the activate sludge subjected to seawater acclimation culture and nitrification (AMNS).

When the incubation tank is allowed to stand, bacterial flocks are confirmed and, since their specific gravity are heavier than sea water, most of the bacterial flocks are precipitated. That is not noted in the pure culture using each of ammonia oxidizing bacteria and nitrite oxidizing bacteria but is observed in a mixed culture using activated sludge as a raw material. When the flocks of AMNS was observed under a microscope, the sludge was found to be composed of flocks having a diameter of 50–100 $\mu$m. Further, when AMNS was observed under a scanning electron microscope (SEM), it was found that the inner area of the sludge flocks contained granules comprising filamentous fungi and tacky substances of 20–100 $\mu$m. When SV30 and SVI of AMNS were determined, they were 9% and 42.6, respectively and an excellent sedimentation property was noted. Accordingly, it has been clarified that, even from the sludge from excrement treatment plant diluted with seawater, nitrified activated sludge having a high activity in sea water (and, of course, in fresh water as well) was able to be produced in a large quantity within a very short period.

The advantages of the mixed culture using activated sludge as a raw material as compared with the pure culture using each ammonia oxidizing bacteria or nitrite oxidizing bacteria solely will be as follows.

In a pure culture system, each of ammonia and nitrous acid is necessary as an energy substrate separately but, in a mixed culture system, only ammonia may be supplied as an energy substrate.

In addition, in a pure culture system, it is quite difficult to make the bacterial cells grown in a high concentration but, in a mixed culture system, it is easy that they are grown to such an extent that the medium is suspended. This presumably because of ecology of the ammonia oxidizing bacteria and the nitrite oxidizing bacteria that they form neither colonies nor flocks in the same group but take a floating life.

Incidentally, the marine nitrifying bacteria obtained as such have been deposited at the National Institute of Bioscience and Human Technology, Agency of Industrial and Technology (Accession No.: FERM BP-7150; Identifying Indication: BICOM Nitrifying Bacteria SWAQ SP-78).

High-Concentration Incubation of Denitrifying Bacteria (Manufacture of Denitrifying Activated Sludge)

Figure 4:
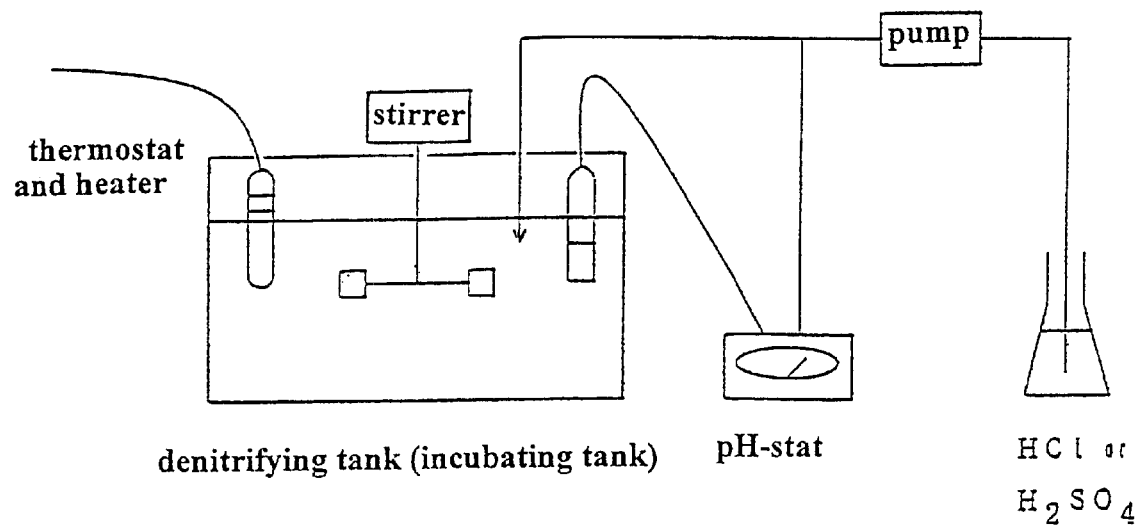
FIG. 4 is a simplified illustrative drawing which shows an example of the apparatus for denitrification and acclimation culture of the activated sludge.

A batch incubation was carried out using an incubation tank of a fill-and-draw type as shown in FIG. 4 where one cycle comprised two days.

Thus, 12 liters of activated sludge of an excrement sewage plant diluted with sea water were placed in a denitrifying tank and then diluted with sea water to an extent of 20 liters. After that, a liquid subjected to nitrification and acclimation culture (a liquid containing $NO_3$—N) generated by incubation of nitrifying bacteria and methanol which was in a 3-fold concentration of $NO_3$—N concentration were placed therein.

The denitrifying tank was set in such a manner to keep at 27° C. using a thermostat and a heater and to maintain the rising pH at 7.5–8.5 using a pH controller and an incubation promoter. Stirring was carried out at 70 rpm using a stirrer, the sludge was precipitated for one hour on the second day, the supernatant liquid was removed, a liquid subjected to nitrification and acclimation culture containing methanol in a three-fold concentration to the $NO_3$—N concentration was poured therein and the stirring was started again. Since the initial salt concentration of the sludge was 75% to sea water, an acclimation culture with sea water was initiated from the stage where the sea water ratio was 75%.

Figure 5:
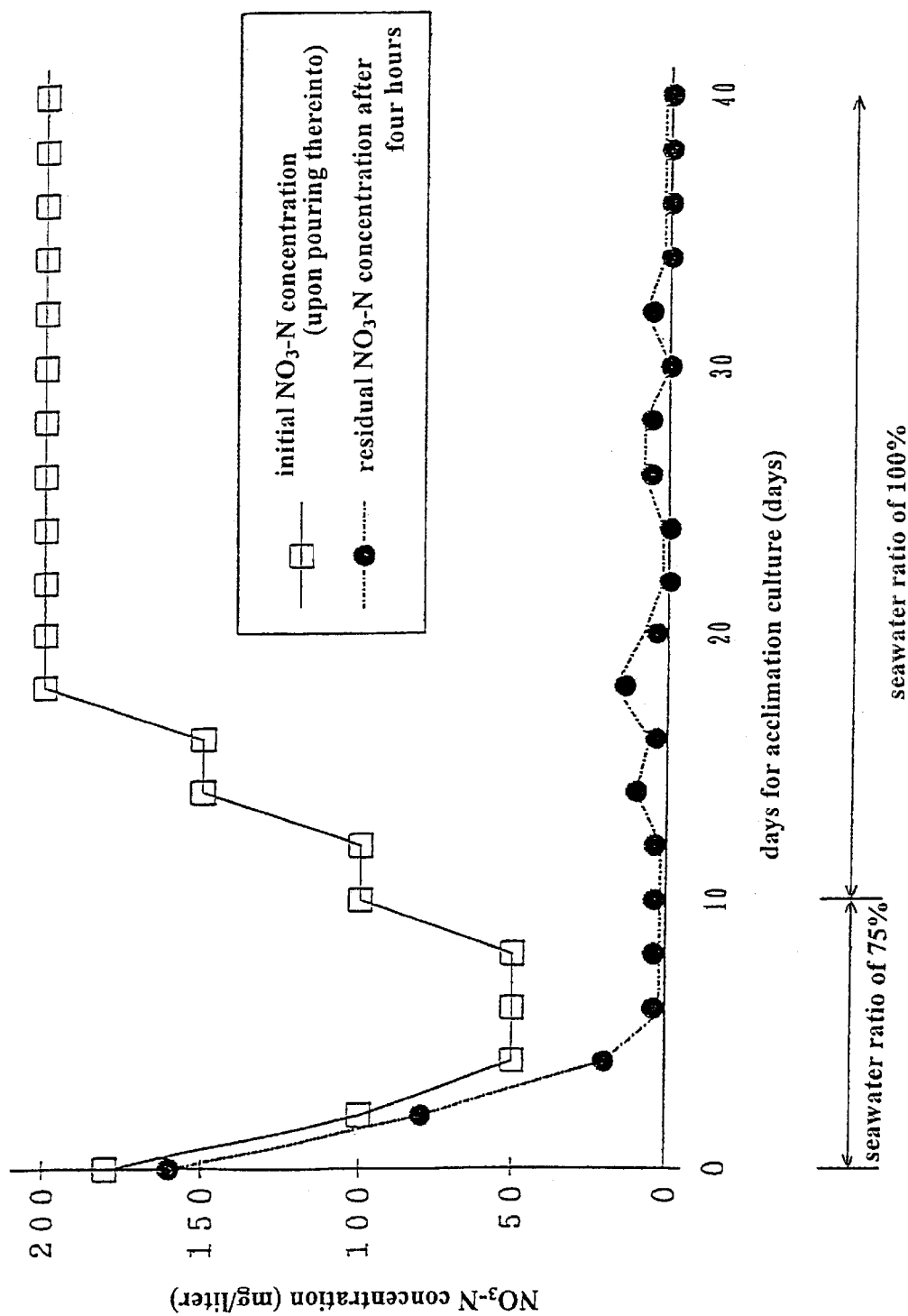
FIG. 5 is a graph which shows the changes in concentration of NO$_3$—N with a lapse of time during the process of denitrification and acclimation culture of the activated sludge.

FIG. 5 shows a process of a seawater acclimation culture of the sludge from an excrement treatment plant. The said drawing shows the initial $NO_3$—N concentration, the residual $NO_3$—N concentration after four hours from the incubation and the seawater ratio. At the stage when the $NO_3$—N concentration of 100 mg/liter was completely denitrified after one day from the incubation, the sea water ratio was raised to 100%. After ten days from the acclimation culture, 100 mg/liter of $NO_3$—N were almost completely denitrified after one day from the incubation and, therefore, the sea water ratio was raised to 100% and, further, in order to increase the activity of the denitrified activated sludge and the concentration of MLSS, the initial $NO_3$—N concentration was raised to 150 mg/liter and to 200 mg/liter.

As a result, it was possible on the 25th day of the acclimation culture with sea water and thereafter (within one month) to prepare an activated sludge subjected to seawater acclimation culture and denitrification (AMDS) which was able to denitrify and remove 200 mg/liter of $NO_3$—N for incubation of four hours.

Denitrifying rate of the sludge from an excrement treatment plant before the acclimation culture and denitrifying rate of AMDS were calculated from the following formula and shown in the following Table2. The changing rate was determined from the inclination of the section where the $NO_3$—N concentration linearly changed within several hours from initiation of the stirring and the value obtained by dividing that by the sludge concentration was defined as a denitrifying rate (refer to the following formula).

$$RNO_3\text{—}N=[(dNO_3\text{—}N)/dt]\cdot[1/S]$$

($RNO_3$—N: $NO_3$—N reducing rate (mg—$NO_3$—N/g-MLSS·hr)

S: concentration of sludge MLSS (g/liter))

TABLE 2

| | Denitrifying Rate | SV30 | SVI |
|---|---|---|---|
| Sludge at Excrement Sewage Plant before Acclimation Culture | 0.39 | — | — |
| Sludge Subjected to Seawater Acclimation Culture and Denitrification (AMDS) | 16.10 | 11% | 34.4 |

*Unit for denitrifying rate: mg-$NO_3$—N/g-MLSS.hr

The result was that, after one month from the seawater acclimation culture, denitrified activated sludge showing a denitrifying activity of 16.1 mg—$NO_3$—N/g-MLSS·hr in sea water was prepared. The denitrifying rate of AMDS is higher to an extent of one order as compared with the specific denitrifying rate (0.04–0.08 g-N/g-MLSS·day) reported for a sewage disposal, etc. and it seems that the denitrifying bacteria are the species having a priority.

Incidentally, the above-mentioned denitrifying activity became 25 mg (or more) —$NO_3$—N/g-MLSS·hr after two months from the seawater acclimation culture.

When AMDS was observed under a scanning electron microscope (SEM), granules of 20–100 μm were found to be formed. When the flocks of AMDS were observed under an optical microscope, many flocks having a diameter of 20–100 μm were present in the sludge. As given in Table 2, SVI and SV30 of AMDS were 34.4 and 11%, respectively and the sedimentation characteristics were good as well.

Incidentally, we planned to deposit the marine denitrifying bacteria prepared as such with the Patent Microorganism Deposit Center, the National Institute of Bioscience and Human Technology, Agency of Industrial and Technology but the deposit was rejected. (A certificate for rejection of the deposit has been received. In the meanwhile, the following institute stores the Identifying Indication of the said marine denitrifying bacteria [BICOM Denitrifying Bacteria SWAQ SP-21] and is prepared to accept the request for sparing them from the third party but, prior to the request for sparing, it is necessary to contract an agreement with the storing institute for the microorganism. A form of the agreement for sparing the microorganism and a form of the request for sparing the microorganism are available from the following institute. "Kabushiki Kaisha Bicom. 16th Floor, Senri Life Science Center, 4-2 Shinsenri Higashimachi-1-chome, Toyonaka-shi, Osaka-fu, Japan (Postal Code: 560-0062); Telephone: 06 4863 7529; Telefax: 06 4863 7509)".

A High-Degree Apparatus for Water Treatment (Nitrifying and Denitrifying Apparatus)

Figure 6:
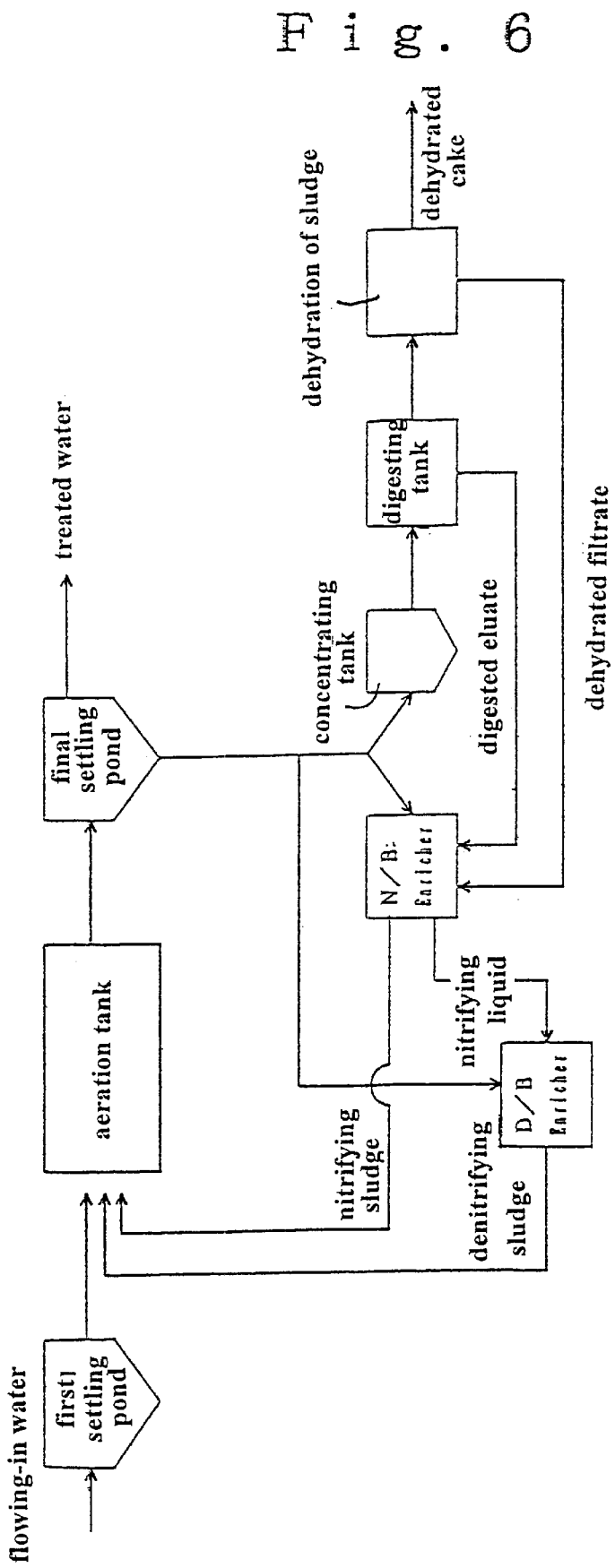
FIG. 6 is a simplified illustrative drawing which shows a highly treating apparatus for water equipped with a capability of significant reduction in the amount (volume) of the activated sludge.

Now, a reduction of weight of sewage sludge and a high-degree water treating system by means of acclimation cultured sludge return method equipped with an acclimation culture tank for nitrifying sludge and a denitrifying sludge acclimation culture tank will be illustrated by referring to FIG. 6.

In a water treatment plant, sewage which is water to be treated containing nitrogen compounds (flowing-in water) is firstly sent to a settling pond and the supernatant liquid is conveyed to an aeration tank. Here, it is subjected to a microbial treatment by a nitrifying activated sludge and a denitrifying activated sludge whereby the nitrogen compounds contained in the flowing-in water are converted to nitrogen gas. The flowing-in water is denitrified as such and conveyed to the final settling pond and its supernatant fluid is discharged as a treated water.

Usually, the precipitate in the final settling pond is returned to an aeration tank as an activated sludge but, in the nitrifying and denitrifying apparatuses of this example, the activated sludge is not returned to an aeration tank but each predetermined amount thereof is conveyed to a nitrifying sludge acclimation culture tank (N/B enricher) and a denitrifying sludge acclimation tank (D/B enricher). Residual activated sludge is sent to a concentrating tank.

As mentioned already, the activated sludge sent to a nitrifying sludge acclimation culture tank (N/B enricher) is subjected to a nitrification and acclimation culture in this acclimation culture tank whereupon nitrifying activated sludge containing a high concentration of nitrifying bacteria is produced (manufactured). Incidentally, as a liquid containing $NH_4$—N at that time, that which is present in a water treatment plant is used. Thus, a digested eluate from the digesting tank and/or a dehydrated filtrate from the sludge dehydrating tank are/is used (cf. FIG. 6).

As mentioned already, the activated sludge conveyed to the denitrifying sludge acclimation culture tank (D/B enricher) is subjected to a denitrification and acclimation culture in this denitrifying sludge acclimation culture tank to produce (manufacture) the denitrifying activated sludge containing a high concentration of denitrifying bacteria. Incidentally, a nitrified liquid generated by the denitrifying sludge acclimation culture tank (N/B enricher) is used as a liquid containing $NO_3$—N at that time.

As mentioned above, the precipitate in the final settling pond has been conventionally returned to an aeration tank but, in the nitrifying denitrifying apparatus of the example of the present invention, the activated sludge is not returned to an aeration tank but conveyed to each of a nitrifying sludge acclimation culture tank and a denitrifying sludge acclimation tank and, in those acclimation culture tanks, only nitrifying bacteria and only denitrifying bacteria are subjected to an enrichment culture in a nitrifying sludge acclimation culture tank and a denitrifying sludge acclimation culture, respectively whereby the action and the advantage that other bacteria die (disappear) and amount (volume) of the activated sludge most occupied by bacteria significantly decreases are achieved.

When the nitrifying activated sludge and the denitrifying activated sludge, each having a high concentration, manufactured as such is returned to an aeration tank, a treatment which is in higher speed and higher efficiency than those in the conventional water treatment can be carried out.

Figure 7:
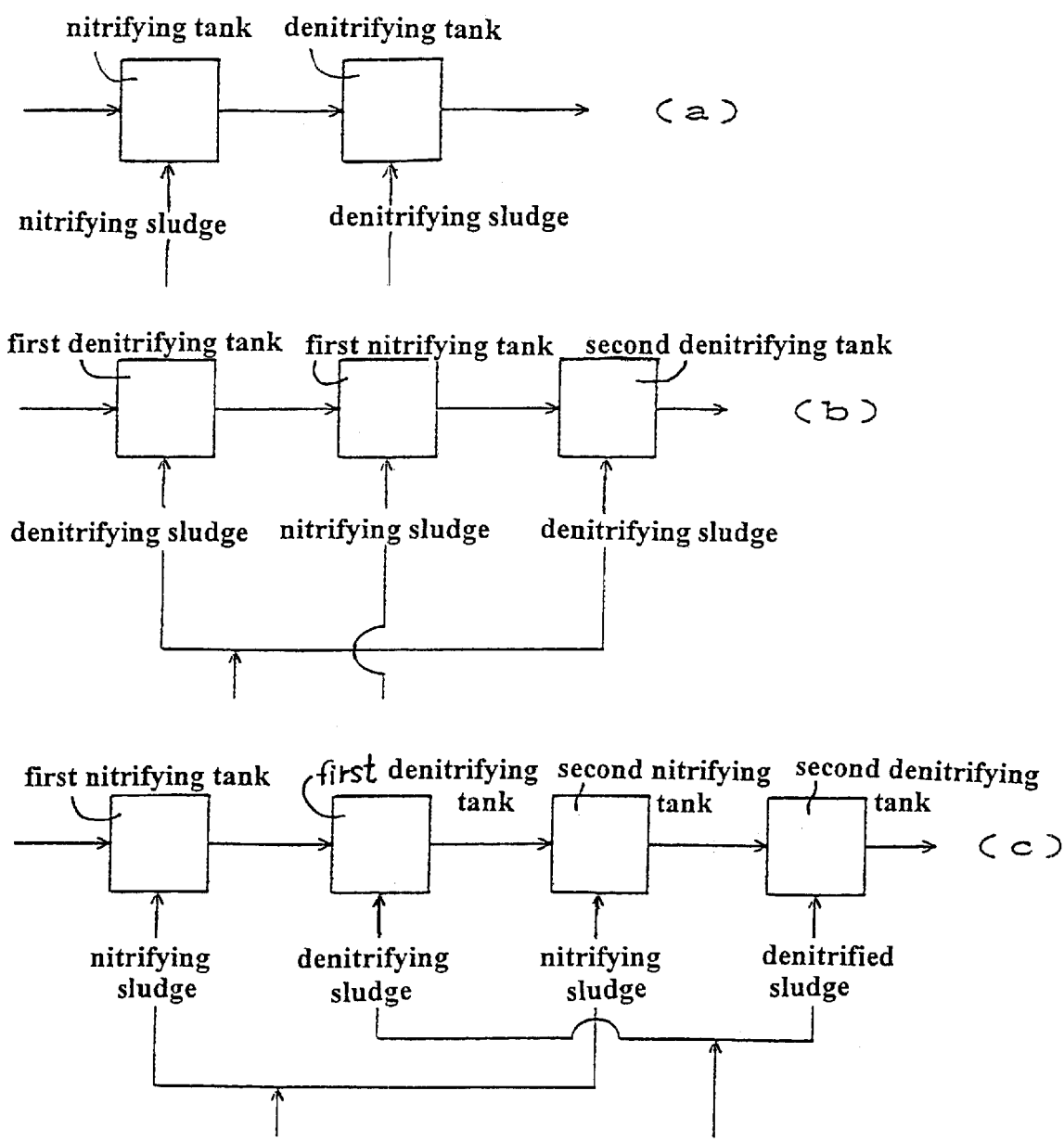
FIG. 7 is a simplified illustrative drawing which shows an example of the embodiment of an aeration tank in the example of the present invention.

The form of the aeration tank may be in the conventionally known ones. For example, as shown in FIG. 7, (a) a form comprising a nitrifying tank and a denitrifying tank; (b) a form comprising the first denitrifying tank, the first nitrifying tank and the second denitrifying tank; and (c) a form where a nitrifying tank and a denitrifying tank are repeatedly arranged may be adopted.

Closed Raising Apparatus on Land

Figure 8:
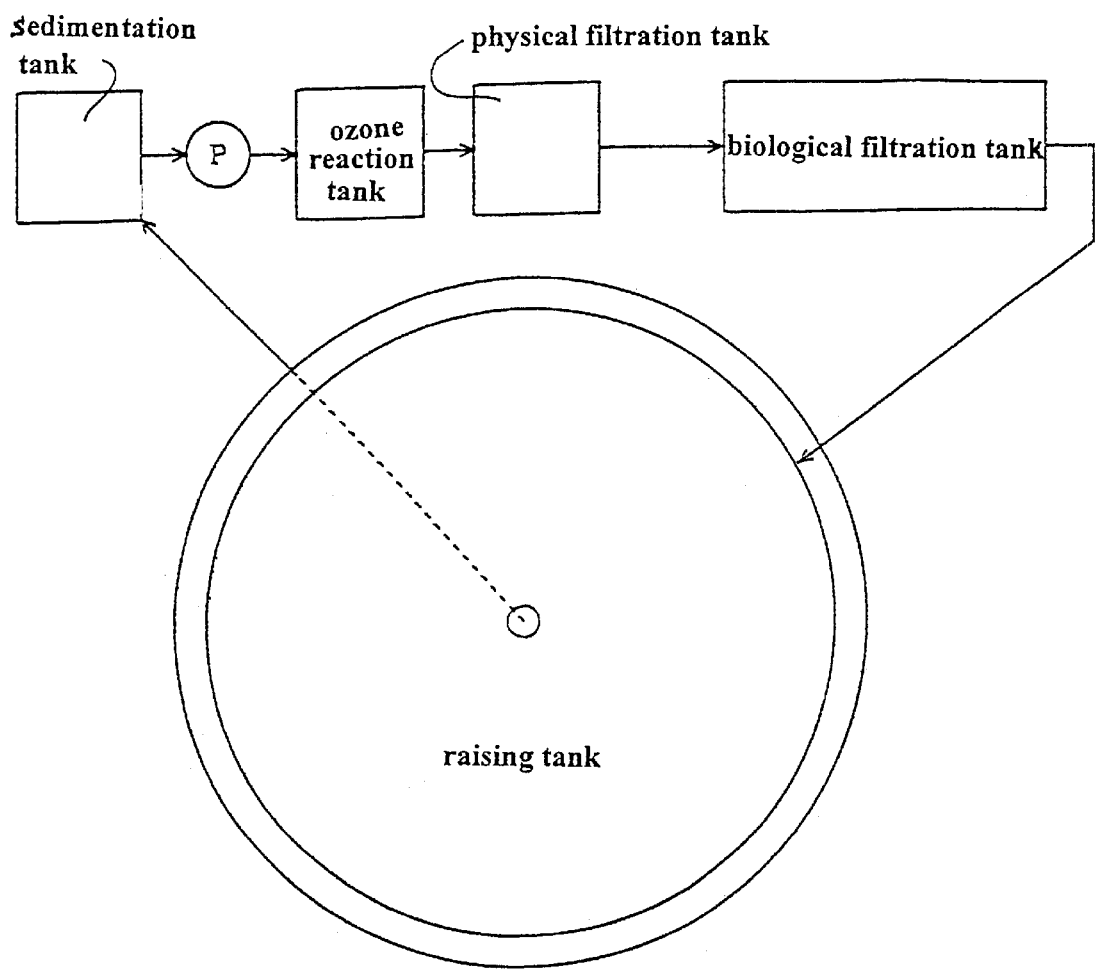
FIG. 8 is a simplified illustrative drawing which shows an example of a closed incubation apparatus on land.

As an example for utilizing the nitrifying activated sludge and the denitrifying activated sludge prepared in the present invention, a closed raising apparatus on land will be illustrated by referring to FIG. 8.

As shown in the drawing, a predetermined amount of sea water is discharged into a sedimentation tank from a raising tank in which many fries of fish such as flatfish, oniokoze (*Inimicus japonicus*) and prawn together with sea water are placed. In this discharged liquid, nitrogen in an ammonia type ($NH_4$—N) is contained. In the sedimentation tank, the solid is sedimented while the supernatant liquid is sent to an ozone reaction tank by a pump and contacts ozone whereupon a sterilizing treatment is carried out.

After that, the sterilized liquid is conveyed to a biological filtration tank via a physical filtration tank. The biological filtration tank consists of at least one nitrifying tank and one denitrifying tank. The above-mentioned nitrifying activated sludge is filled in the above-mentioned nitrifying tank while the above-mentioned denitrifying activated sludge is filled in the denitrifying tank. As shown in FIG. 7, examples of a combination of the nitrifying tank and the denitrifying tank in this biological filtration tank are (a) a form comprising a nitrifying tank and a denitrifying tank, (b) a form comprising the first denitrifying tank, the first nitrifying tank and the second denitrifying tank and (c) a form where a nitrifying tank and a denitrifying tank are repeatedly arranged. When passing through the biological filtration tank, nitrogen of an ammonia type is converted to nitrogen of a nitrate type as a result of oxidation with the nitrifying bacteria which are contained in the nitrifying bacteria in a high concentration and the nitrogen in a nitrate type is further oxidized to nitrogen gas by the denitrifying bacteria contained in the denitrifying activated sludge in a high concentration.

After the nitrogen compound in the discharged water is converted to nitrogen gas as such, it is returned to a raising tank again.

In the closed raising apparatus on land in this example, all environmental conditions such as temperature, dissolved oxygen and pH of a raising water, illumination and water flow can be adjusted and controlled by means of computers in a room such as in a plant and, accordingly, the work therefor requires few hand and a raising cost becomes low whereby it is possible to reduce the production cost. In addition to that, there is no problem of contamination of pathogenic microorganisms such as virus and, further, there is no problem of causing a pollution of sea water. Thus, in the raising which has been carried out up to now, sea water is pumped up either continuously or intermittently and poured into a raising tank and, therefore, there is always a possibility that the raising fish is infected by virus in the sea water. However, according to the closed raising apparatus of this example, water for raising is used by recycling whereby there is no problem of contamination of virus. Further, in the conventional raising method, in order to discard the ammonia which is discharged from the raising fish from a raising tank, the water for raising is to be diluted and directly discarded to the sea. As a result, there is a problem of pollution of sea water due to the drainage of the raising water but, according to the example of the present invention, the water for raising which is discharged (flown out) into sea is substantially nil whereby there is no problem of causing a pollution of the ocean.

Soil Conditioner with an Object of Preservation of Underground Water

Since about 50 years ago, denitrifying bacteria in soil have become little (or entirely nil) whereupon the nitrogen fertilizer applied onto the soil directly moves downward in the soil resulting in a source for pollution of the underground water. Underground water is an important factor for constituting the sound water circulation in an ecosystem and is a precious source for fresh water. Its importance is believed to be more and more increasing when shortage of water and exhaustion of water in recent days are taken into consideration.

When the denitrifying activated sludge prepared by the manufacturing method of the present invention is used, it is possible to prevent the pollution of the underground water by nitrogen fertilizers.

Thus, the denitrifying activated sludge (denitrifying bacteria) which is prepared by the above-mentioned acclimation culture experiment is applied to the soil like agricultural chemicals and then the farmland is plowed by a cultivator. As a result, even when too much nitrogen fertilizers are applied, such excessive nitrogen fertilizers are denitrified by the denitrifying bacteria in the soil and do not come down beneath the plant (cultivated plant) whereby pollution of the underground water by the nitrogen fertilizers can be minimized.

INDUSTRIAL APPLICABILITY

As mentioned herein above, it is now possible in accordance with the present invention to provide a method for the high-concentration incubation of nitrifying bacteria (marine nitrifying bacteria and freshwater nitrifying bacteria) or denitrifying bacteria (marine denitrifying bacteria and freshwater denitrifying bacteria) using activated sludge as a raw material; to provide an incubation promoter to be used for the said method; and to provide a method for the weight-reducing treatment of activated sludge. Thus, it is now possible to incubate the nitrifying bacteria and the denitrifying bacteria in large quantities and in high concentrations which have been believed to be impossible up to now. In addition, the volume of the sludge can be significantly reduced.

What is claimed is:

1. In a method for incubation of nitrifying bacteria which are contained in activated sludge, a method for incubation of nitrifying bacteria comprising subjecting the activated sludge to nitrification and acclimation culture by a liquid containing $NH_4$—N for a predetermined period under such a condition that dissolved oxygen is not less than 2 mg/liter, pH is 7.0–9.0 and temperature is 20–40° C. and, at the same time, constantly maintaining the pH, which is apt to tend to an acid side during the acclimation culture process, within the above-mentioned range by addition of an incubation promoter comprising a mixture of sodium carbonate and sodium hydrogen carbonate whereby the nitrifying bacteria contained in the above-mentioned sludge are subjected to an acclimation culture and accumulated.

2. In a method for the incubation of nitrifying bacteria which are contained in activated sludge, a method for incubation of denitrifying bacteria comprising subjecting the activated sludge to a nitrification and an acclimation culture by a liquid containing $NH_4$—N for a predetermined period under such a condition that the dissolved oxygen is not more than 5 mg/liter and, at the same time, constantly maintaining the pH, which is apt to tend to an acid side during the acclimation culture process, within the above-mentioned range by addition of an incubation promoter comprising a mixture of sodium carbonate and sodium hydrogen carbonate whereby the denitrifying bacteria contained in the above-mentioned activated sludge are subjected to an acclimation culture and accumulated.

3. The incubation of the nitrifying bacteria according to claim 1 or 2, wherein the said liquid containing $NH_4$—N is a waste liquid from the treatment of sludge.

4. The incubation of the nitrifying bacteria according to claim 3, wherein the ammonia concentration in the said sludge-treated liquid is 100–300 mg/liter.

5. The high-concentration incubation of nitrifying bacteria according to claim 3, wherein said waste liquid from the treatment of sludge is dehydrated sludge filtrate or digested eluate.

6. The incubation of the nitrifying bacteria according to claim 1 or 2, wherein the above-mentioned dissolved oxygen is 2–5 mg/liter, the pH is 7.5–8.5 and the temperature is 25–35° C.

7. The incubation of the nitrifying bacteria according to claim 1 or 2, wherein the mixing ratio of sodium carbonate to sodium hydrogen carbonate in the said mixture is 4–7:4–8 in terms of a molar ratio.

8. The incubation of the nitrifying bacteria according to claim 1 or 2, wherein the said activated sludge is a sludge diluted with sea water.

9. In a method for incubation of denitrifying bacteria which are contained in activated sludge, a method for incubation of nitrifying bacteria comprising subjecting the activated sludge to denitrification and acclimation culture by a liquid containing $NO_3$—N for a predetermined period under such a condition that dissolved oxygen is not less than 2 mg/liter, pH is 6.0–9.0, temperature is 10–40° C. and ROH (R is $CH_3$— and/or $C_2H_5$—) is present as an external carbon source whereby the denitrifying bacteria contained in the said activated sludge are subjected to an acclimation culture and accumulated.

10. The incubation of the denitrifying bacteria according to claim 9, wherein the said activated sludge is a sludge which is diluted with sea water.

11. The incubation of denitrifying bacteria according to claim 1, 2 or 9, wherein said activated sludge is sewage sludge or excrement sludge.

12. The incubation of the denitrifying bacteria according to claim 9, wherein the said liquid containing $NO_3$—N is a liquid from the treatment of nitrification and acclimation culture generated by carrying out incubation of the nitrifying bacteria comprising subjecting the activated sludge to nitrification and acclimation culture by a liquid containing $NH_4$—N for a predetermined period under such a condition that dissolved oxygen is not less than 2 mg/liter, pH is 7.0–9.0 and temperature is 20–40° C. and, at the same time, constantly maintaining the pH, which is apt to tend to an acid side during the acclimation culture process, within the above-mentioned range by addition of an incubation promoter comprising a mixture of sodium carbonate and sodium hydrogen carbonate whereby the nitrifying bacteria contained in the above-mentioned sludge are subjected to an acclimation culture and accumulated.

13. The incubation of the denitrifying bacteria according to claim 9, wherein the said liquid containing $NO_3$—N is a liquid from the treatment of nitrification and acclimation culture generated by carrying out incubation of the nitrifying bacteria comprising subjecting the activated sludge to nitrification and acclimation culture by a liquid containing $NH_4$—N for a predetermined period under such a condition that dissolved oxygen is not less than 2 mg/liter, pH is 7.0–9.0 and temperature is 20–40° C. and, at the same time, constantly maintaining the pH, which is apt to tend to an acid side during, the acclimation culture process, within the above-mentioned range by addition of an incubation promoter comprising a mixture of sodium carbonate and sodium hydrogen carbonate whereby the nitrifying bacteria contained in the above-mentioned sludge are subjected to an acclimation culture and accumulated.

14. The incubation of the denitrifying bacteria according to claim 9, 12 or 13, wherein the external carbon source ROH is added so that the said ROH (mg/liter)/$NO_3$—N (mg/liter) becomes 3.0 or more.

15. A promoter for incubation of nitrifying bacteria which restores changing pH during an acclimation culture period to a predetermined range and also acts as a carbon source in carrying out the acclimation culture of an activated sludge for a predetermined period by a waste liquid treated with sludge for incubation of the nitrifying bacteria contained in the activated sludge, the promoter comprising a mixture of sodium carbonate and sodium hydrogen carbonate.

16. A promoter according to claim 15, wherein said waste liquid from the treatment of sludge is dehydrated sludge filtrate or digested eluate.

17. A method for a weight-reduction treatment of activated sludge comprising subjecting the activated sludge to nitrification and acclimation culture by a liquid containing $NH_4$—N for a predetermined period under such a condition that the dissolved oxygen is not less than 2 mg/liter, the pH is 7.0–9.0 and the temperature is 20–40° C. and, at the same time, constantly maintaining the pH, which is apt to tend to an acid side during the acclimation culture process, within the above-mentioned range by addition of an incubation promoter comprising a mixture of sodium carbonate and sodium hydrogen carbonate.

18. A method for a weight-reduction treatment of activated sludge, comprising subjecting the activated sludge to a denitrification and acclamation culture by a liquid containing $NO_3$—N for a predetermined period under such a condition that the temperature is 10–40° C., the pH is 6.0–9.0, the dissolved oxygen is not less than 2 mg/liter and ROH, R being $CH_3$— and/or $C_2H_5$—, is present as an external carbon source.

19. A method according to claim 17 or 18, wherein said waste liquid from the treatment of sludge is dehydrated sludge filtrate or digested filtrate.

20. In method for the manufacture of a nitrifying activated sludge containing nitrifying bacteria, a method for the manufacture of nitrifying bacteria containing the nitrifying bacteria comprising subjecting the activated sludge to nitrification and acclimation culture by a liquid containing NH4—N for a predetermined period under such a condition that the dissolved oxygen is not less than 2 mg/liter, the pH is 7.0–9.0 and the temperature is 20–40° C. and, at the same time, constantly maintaining, the pH, which is apt to tend to an acid side during the acclimation culture process, within the above-mentioned range by addition of an incubation promoter comprising a mixture of sodium carbonate and sodium hydrogen carbonate whereby the nitrifying bacteria contained in the above-mentioned sludge are subjected to an acclimation culture and accumulated.

21. In method for the manufacture of a denitrifying activated sludge containing denitrifying bacteria, a method for the manufacture of denitrifying bacteria containing the denitrifying bacteria comprising subjecting the activated sludge to denitrification and acclimation culture by a liquid containing $NO_3$—N for a predetermined period under such a condition that the dissolved oxygen is not less than 2 mg/liter, the pH is 6.0–9.0 of pH, the temperature is 10–40° C. and ROH (R is $CH_3$— and/or $C_2H_5$—) is present as an external carbon source whereby the denitrifying bacteria contained in the said sludge are subjected to an acclimation culture and accumulated.

22. A soil conditioner comprising the denitrifying activated sludge prepared by the method of claim 21.

* * * * *